United States Patent
Gerner et al.

(10) Patent No.: US 6,734,961 B2
(45) Date of Patent: May 11, 2004

(54) FLOW CELLS UTILIZING PHOTOMETRIC TECHNIQUES

(75) Inventors: Yuri Gerner, Mendota Heights, MN (US); Carl W. Sims, St. Paul, MN (US); Thomas J. Thielen, Plymouth, MN (US)

(73) Assignee: Systec, Inc., New Brighton, MN (US)

( * ) Notice: Subject to any disclaimer, the term of this patent is extended or adjusted under 35 U.S.C. 154(b) by 29 days.

(21) Appl. No.: 10/068,683

(22) Filed: Feb. 6, 2002

(65) Prior Publication Data

US 2003/0174322 A1 Sep. 18, 2003

Related U.S. Application Data (63) Continuation-in-part of application No. 09/765,497, filed on Jan. 18, 2001.

(51) Int. Cl.$^7$ .............................. G01N 1/10; G01N 21/00
(52) U.S. Cl. ........................................ 356/246; 356/436
(58) Field of Search ................................. 356/436, 246; 250/573, 576, 239, 227.25; 422/104, 102, 82.05, 82.09; 385/12, 125

(56) References Cited

U.S. PATENT DOCUMENTS

| | | |
|---|---|---|
| 3,795,450 A | 3/1974 | Munk |
| 3,954,341 A | 5/1976 | Uffenheimer |
| 4,260,257 A | 4/1981 | Neeley et al. |
| 4,530,569 A | 7/1985 | Squire |
| 4,571,078 A | 2/1986 | Capps, II |
| 4,575,424 A | 3/1986 | Allington et al. |
| 4,754,009 A | 6/1988 | Squire |
| 4,816,123 A | 3/1989 | Ogan et al. |
| 4,867,559 A | 9/1989 | Bach |
| 4,886,356 A | 12/1989 | Paradis |
| 4,889,611 A | 12/1989 | Blough, Jr. |
| 4,973,142 A | 11/1990 | Squire |
| 4,975,505 A | 12/1990 | Squire |
| 4,977,025 A | 12/1990 | Squire |
| 4,999,248 A | 3/1991 | Squire |
| 5,000,547 A | 3/1991 | Squire |
| 5,006,382 A | 4/1991 | Squire |
| 5,061,024 A | 10/1991 | Keys |
| 5,076,659 A | 12/1991 | Bekiarian et al. |
| 5,120,129 A | 6/1992 | Farquharson et al. |
| 5,140,169 A | 8/1992 | Evens et al. |
| 5,153,679 A | 10/1992 | Gilby |
| 5,184,192 A | 2/1993 | Gilby et al. |
| 5,267,341 A | 11/1993 | Shearin |
| 5,404,217 A | 4/1995 | Janik et al. |
| 5,416,879 A | 5/1995 | Liu |
| 5,444,807 A | 8/1995 | Liu |
| 5,570,447 A | 10/1996 | Liu |
| 5,604,587 A | 2/1997 | Che et al. |
| 5,608,517 A | 3/1997 | Munk |
| 5,822,067 A | 10/1998 | Yanik |
| 5,847,835 A | 12/1998 | Fukunaga |

(List continued on next page.)

Primary Examiner—Zander V. Smith
Assistant Examiner—Gordon J. Stock, Jr.
(74) Attorney, Agent, or Firm—Haugen Law Firm LLP (57) ABSTRACT

A flow cell for transporting fluid in a radiant energy field includes a cell structure having a tube extending therethrough including a radiant energy blocking portion integral therewith. In a particular embodiment, the cell structure includes one or more end caps having a protrusion extending therefrom, wherein the protrusion may be inserted into the tube to create a fluid seal, the end caps including open channels for transporting fluid and radiant energy therethrough, and the tube in the cell structure includes an efficient radiant energy transmission lining that is spaced from the end cap protrusions, thereby forming a gap volume in the flow cell open channel, which gap volume may be calibrated such that radiant energy losses may be standardized in respective flow cells transporting fluids having various indexes of refraction.

20 Claims, 4 Drawing Sheets

U.S. PATENT DOCUMENTS

| | | |
|---|---|---|
| 5,854,863 A | 12/1998 | Erb et al. |
| 5,883,721 A | 3/1999 | Gilby et al. |
| 5,917,606 A | 6/1999 | Kaltenbach |
| 6,011,882 A | 1/2000 | Dasgupta et al. |
| 6,016,372 A | 1/2000 | Fein et al. |
| 6,020,207 A | 2/2000 | Liu |
| 6,177,518 B1 * | 1/2001 | Lahijani .................... 525/199 |

* cited by examiner

Fig.-1

FLOW CELLS UTILIZING PHOTOMETRIC TECHNIQUES

CROSS-REFERENCE TO RELATED APPLICATION

The present application is a continuation-in-part of our copending application Ser. No. 09/765,497, filed Jan. 18, 2001, entitled "FLOW CELLS UTILIZING PHOTOMETRIC TECHNIQUES" and which is assigned to the same assignee as the present application.

FIELD OF THE INVENTION

The present invention relates to flow cells generally, and more particularly to radiant energy flow cells for use in various analytical chemistry applications, such as spectrophotometry. This invention also relates to methods for fabricating such flow cells.

BACKGROUND OF THE INVENTION

Numerous devices have been designed and implemented for use in preparing and testing samples in various environments, particularly in analytical chemistry applications. One such device is a flow cell, which may be used to transport samples to and through analytical instruments such as spectrophotometers for analysis purposes. Flow cells have typically been utilized to transport liquid samples, but other flowable sample types have also been implemented.

Most commonly, flow cells have been implemented to transport sample solutions through a volume disposed between a radiant energy source and an energy detector, which detector measures the relevant energy absorption or transmission through the sample solution. An example of such a detector is a spectrophotometer. Various analytical instruments then interpret the resultant energy "fingerprints" or transmitted vs. absorbed wavelengths to decipher sample constituents.

To efficiently pass the energy through the sample solution, however, the flow cell walls typically use focusing optics such that energy impact upon the flow cell walls is minimized. Without such focusing optics, previous flow cell configurations called for the sample solvating fluid to have a higher index of refraction than materials commonly used in the flow cell walls. As a result, organic fluids were typically utilized as solvents in flow cell applications prior to the incorporation of focusing optics.

For several reasons, however, aqueous fluid carriers have been sought as a preferred alternative to such organic fluids. To implement a flow cell system utilizing an aqueous fluid, a material having an index of refraction less than that of water is needed for the respective flow cells. One such material is a perflourinated copolymer developed by DuPont of Wilmington, Del., under the trade name Teflon AF™. Thus, analytical flow cells preferably include a layer of Teflon AF™ or other low index of refraction material to allow efficient radiant energy propagation in spectrophotometry and photometry applications.

An additional issue encountered by current flow cell systems is the transmission of stray light through the cell to a photometric detector downstream therefrom. Generally speaking, stray light is light which is perceived by the photometric detector without first passing through the sample being analyzed. Such stray light is most often a result of light transmitting directly through transparent or translucent flow cell material without passing through the sample path. As stated above, flow cell systems are specifically designed to maximize internal reflection of photometric radiation through the flow cell to the detector. Such systems simultaneously attempt to minimize source light from entering directly into an end of the flow cell wall to correspondingly minimize stray light reaching the detector. On large scale systems, mechanical photomasking devices have been implemented to block at least incoming light from entering an end of the flow cell wall. As flow cell systems become ever smaller, however, such mechanical photomasking devices become extremely difficult to effectively block stray light while allowing sample radiant energy transmission to pass therethrough into the core of the flow cell.

Most flow cells in use today generally do not embody efficient and reliable designs. Many employ multi-sectional, multi-directional tubes which may cause "dead flow" zones, and may introduce an increased risk of fluid leakage. Other flow cell designs are undesirably complex, are difficult to implement in current analytical instrument geometries, or are excessively expensive to produce.

Accordingly, it is a principle object of the present invention to provide an improved means for exposing a sample solution to a radiant energy field used for analyzing sample composition.

It is a further object of the present invention to provide an improved flow cell design yielding desired sample solution flow characteristics.

It is another object of the present invention to provide a flared-tube flow cell design which reduces flow turbulence through the flow cell.

It is a yet further object of the present invention to provide a flow cell having a calibrated gap volume for standardizing radiant energy losses among various fluids flowing through a radiant energy field.

It is a still further object of the present invention to provide an improved flow cell including an end cap having a substantially conical frustum portion which engages the flow cell to form a sealed fluid passageway.

It is a further object of the present invention to provide an improved flow cell having end caps which are sized and configured to form high-pressure fluid seals when engaged with a flow cell body.

It is a yet further object of the present invention to provide end caps for a flow cell, wherein the end caps include passageways for fluid and radiant energy transport, and improved sealing means for sealing relationship with the flow cell.

It is a yet further object of the present invention to provide a flow cell having improved radiant energy transmission characteristics.

It is another object of the present invention to provide a flow cell having improved photomasking characteristics for minimizing or eliminating stray light received by the detector.

It is a further object of the present invention to provide a flow cell having partially opaque walls for minimizing stray light transmission through such walls.

It is a still further object of the present invention to provide an improved flow cell for use in HPLC applications.

It is a yet further object of the present invention to provide a method for fabricating flow cells having improved sealing and fluid transport characteristics.

It is a further object of the present invention to provide a method for fabricating flow cells utilizing extruded tubing.

SUMMARY OF THE INVENTION

By means of the present invention, an improved flow cell is contemplated for use in transporting sample fluids in radiant energy fields. Such a flow cell introduces a structure for improved fluid sealing and fluid flow characteristics.

One embodiment of the flow cell of the present invention preferably includes a cell structure having a first elongated tube disposed therein which forms a continuous passageway through the cell structure. The tube includes a radiant energy-blocking portion integral therewith for minimizing passage of stray light through the tube. Attached to the flow cell is at least one end cap that is sealingly engagable with the cell structure. The end cap preferably includes a substantially conical frustum portion extending outwardly therefrom. When assembled, the conical frustum portion preferably extends at least partially into the first open channel.

A first open channel within the first tube is preferably clad with one or more layers forming concentric tubes. Preferably, the innermost tube is a low index of refraction material such as perfluorinated copolymer. A second tube preferably comprising PEEK substantially concentrically surrounds the first tube. Preferably, a third tube comprising FEP substantially concentrically surrounds the PEEK tube, and is in intimate contact with an outer wall of the first open channel. As assembled, the conical frustum portion of the end caps preferably displace a portion of the FEP tube against the first open channel wall, thereby forming a fluid-tight seal between the FEP tube and the conical frustum portions.

Preferably, the end caps include one or more open channels for transporting the sample fluid and the radiant energy. In preferred embodiments, the radiant energy channels are in substantial alignment with the first open channel within the cell structure. The radiant energy channels and the fluid channels preferably merge such that the radiant energy may pass through the sample fluid.

At least one end of the innermost tube is preferably flared outwardly to more efficiently transport the radiant energy and sample fluid. The flared portion of the innermost tube is calibrated so that an internal dimension of the innermost tube may be reduced without significant radiant energy losses, and further enables a reduction in fluid flow turbulence. Such reduced flow turbulence increases the reliability of photometric sample analysis.

In another aspect of the present invention, a gap volume is provided between the first open channel within the cell structure and fluid channels within respective end caps. The gap volume is preferably and adjustably calibrated to define an appropriate volume such that radiant energy losses among various fluids having distinct indexes of refraction may be standardized.

The present invention also contemplates a method for determining sample composition through radiant energy interaction with the sample fluid utilizing the structural elements described above.

DETAILED DESCRIPTION OF THE PREFERRED EMBODIMENTS

The objects and advantages enumerated above together with other objects, features and advances represented by the present invention will now be presented in terms of detailed embodiments described with reference to the attached drawing figures which are intended to be representative of various possible configurations of the invention. Other embodiments and aspects of the invention are recognized as being within the grasp of those having ordinary skill in the art.

Figure 1:
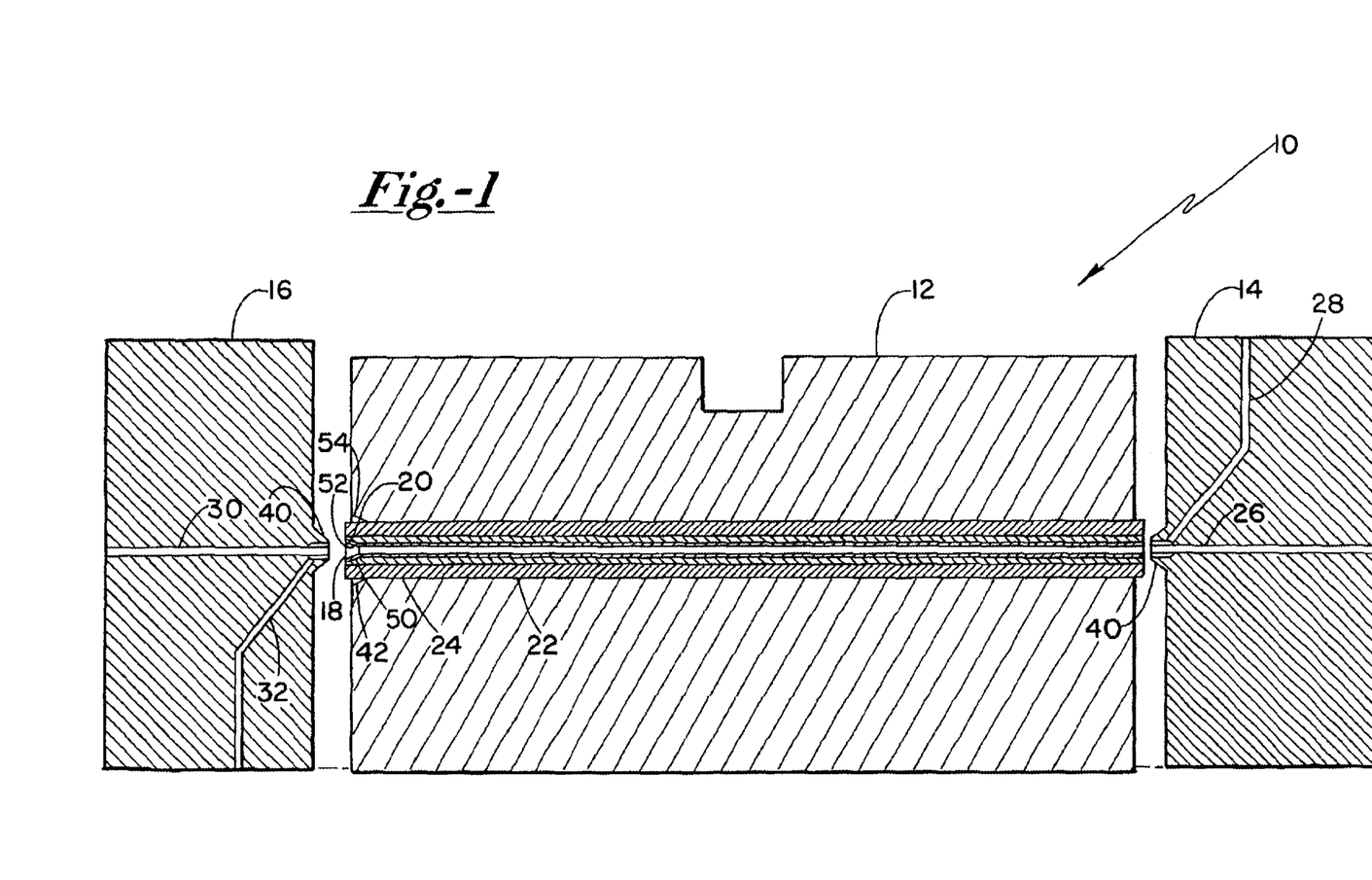
FIG. 1 is a partially exploded cross-sectional view of a flow cell of the present invention.

Referring now by characters of reference to the drawings, and first to FIG. 1, a partially exploded cross-sectional view of a flow cell 10 of the present invention is shown. Flow cell 10 includes cell body 12, and first and second end caps 14, 16 respectively. Cell body 12 preferably includes a first open channel 18 extending therethrough to form a continuous passageway through a length of the cell body. One or more distinct material layers preferably surround open channel 18. Such layers preferably concentrically surround open channel 18, so as to form concentric tubes, an inside diameter of the innermost tube thereby defining open channel 18. The concentricity of respective layers is preferably tightly controlled.

In a preferred embodiment, a first layer 20 of relatively low index of refraction material concentrically surrounds open channel 18. A low refractive index material is desired for use in the first layer 20 so that radiant energy passing through sample fluids in channel 18 is able to propagate over relatively long distances with little deterioration. Flow cell applications employing spectrophotometers or other instruments to analyze fluid composition require that the tube walls within which the fluid and radiant energy pass preferably possess an index of refraction less than that of the fluid to allow efficient propagation of the radiant energy (by a phenomenon known as full internal reflection). Thus, if water is to be used as a base fluid for sample analysis in high-performance liquid chromatography or other analytical chemistry applications utilizing flow cells where internal walls are in contact with the fluid, the internal wall material preferably has an index of refraction less than that of water.

Such an application is contemplated for the present invention. An example of such a low refractive index material is a perfluorinated copolymer such as Teflon AF™, developed and sold by E. I. DuPont deNemours Corp. of Wilmington, Del. At present, Teflon AF™ is the most preferred material for use in the first layer 20 because it is the only material readily available that has an index of refraction lower than that of water or other solvents used in sample analysis, and because it is chemically compatible with most of these solvents. Thus, first layer 20 preferably comprises a perfluorinated copolymer. Preferably, an inner surface of such first layer 20 is relatively free of imperfections, and any imperfections present are preferably smaller than the radiant energy wavelength.

Preferably, first layer 20 is sufficiently thick to prevent radiant energy losses caused by radiant energy penetration through the first layer. As radiant energy is transported through first open channel 18 of cell body 12, the radiant energy penetrates first layer 20 as an evanescent wave, the intensity of which decays exponentially with the depth of first layer 20. For efficient radiant energy transmission through open channel 18, the thickness "T" of first layer 20 should be larger than the penetration depth "δ" of the radiant energy incident thereon. Such depth is given by the following equation, where $n_T$ is the refractive index of first layer 20, $n_i$ is the refractive index of the sample fluid, $\lambda_i$ the wavelength of the incident radiant energy, and i is the radiant energy angle of incidence into channel 18.

$$\delta = \left( \frac{2\pi}{\lambda i} \sqrt{ \frac{\sin^2(i)}{\left(\frac{n_T}{n_i}\right)^2} - 1 } \right)^{-1}$$

In preferred embodiments of the invention, first layer 20 has a thickness of at least two wavelengths of the respective radiant energy passing through open channel 18. Most preferably, first layer 20 is at least 15 μm thick.

In some embodiments, first layer 20 is tubular in form, and preferably forms the boundary defining a course of travel for fluid and radiant energy through cell body 12.

In preferred embodiments of the present invention, second and third layers 22, 24, respectively, are disposed concentrically around first layer 20. Second and third layers 22, 24 are preferably polymeric materials, and are preferably tubular in form. In a particularly preferred embodiment, second layer 22 is PEEK, and third layer 24 is FEP. As shown in FIG. 1, second layer 22 is interposed between first layer 20 and third layer 24, and may be in intimate contact with both first layer 20 and third layer 24. In preferred embodiments, clearance between first, second, and third layers, respectively, is maintained at no greater than 2% of an inner dimension of channel 18.

In preferred embodiments and as illustrated in FIG. 1, third layer 24 is substantially concentrically surrounded by the remainder of cell body 12, which is preferably a rigid, non-corrodable material such as stainless steel. Other materials, however, may be used in place of the exemplary stainless steel.

First and second end caps 14, 16 preferably include at least one open channel extending therethrough. Second open channel 26 is preferably disposed in first end cap 14, and is preferably in alignment with first open channel 18. Similarly, a third open channel 30 is disposed in end cap 16, and is in alignment with channel 18. As shown in FIG. 1, second and third open channels 26 and 30 preferably extend through an entire length of end caps 14 and 16 respectively. Preferably, channels 26, 30 are utilized for transporting radiant energy through flow cell 10, and are desirably disposed in a single plane to eliminate measurement errors which could result from various angled reflection characteristics. In preferred embodiments, channels 26, 30 are fabricated from a material efficient in transporting radiant energy, such as, for example, fiber optic material. A particularly preferred material for use in channels 26, 30 is a quartz fiber optic. Preferably, then, channels 26, 30 are in a direct, straight-line alignment with channel 18. Most preferably, first, second, and third layers 20, 22, 24, respectively, are substantially in concentric alignment with channels 26, 30, and have an offset of no greater than 5% of an inner dimension of channel 18.

In a particular embodiment of the invention, photomasking is utilized to minimize or block stray light passing through flow cell 10 without passing through the sample fluid. In flow cell embodiments having a relatively small inner dimension of channel 18, mechanical light masking of layers 20, 22, 24, but particularly layer 20, becomes extremely difficult. Therefore, at least a portion of layer 20 is made opaque to effectively block stray light passing therethrough.

Figure 2:
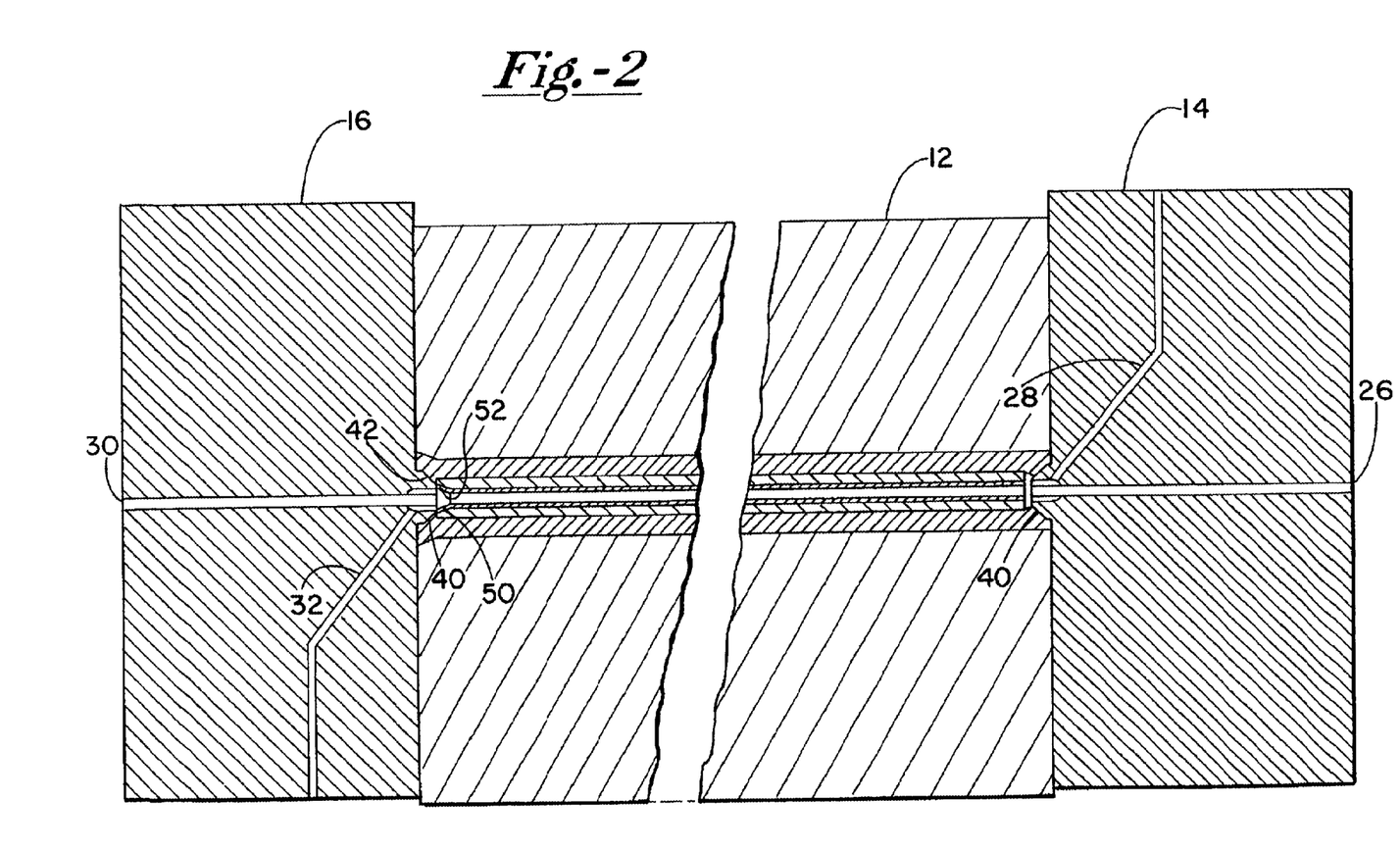
FIG. 2 is a cross-sectional view of the flow cell shown in FIG. 1.
Figure 3:
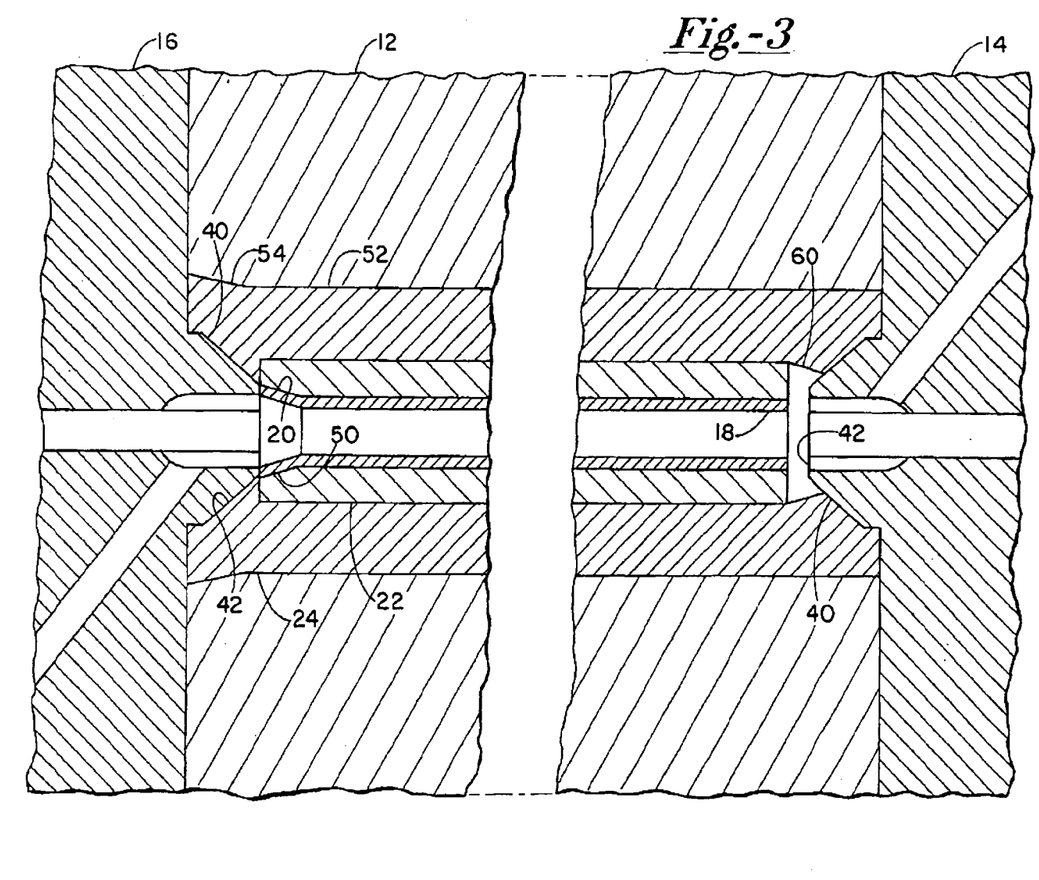
FIG. 3 is an enlarged cross-sectional view of the flow cell shown in FIG. 2.

As shown in FIGS. 1–3, radiant energy is directed through open channels 30, 18, and 26, respectively. Though open channel 18 is preferably mechanically aligned with channels 30 and 26 such that radiant energy may pass directly through the channel without scattering beyond respective boundaries thereof, a portion of the emitted radiation may undesirably pass through one or more of layers 20, 22, and 24 without passing through the sample fluid within channel 18. Most typically, however, any such stray light not passing through the sample fluid between channels 30 and 26 passes through layer 20.

Figure 4:
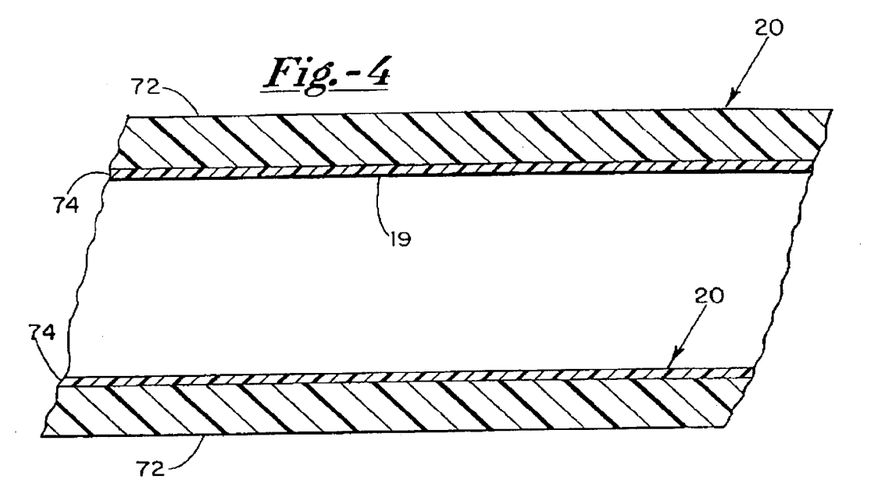
FIG. 4 is a cross-sectional view of tubing including a radiant energy-blocking portion disposed along a length thereof.

As stated above, layer 20 is preferably manufactured from a perfluorinated copolymer such as Teflon AF for particular index of refraction characteristics. To overcome the difficulties associated with mechanically masking relatively small flow cell applications, layer 20 is preferably impregnated or coated with light blocking material. As shown in FIG. 4, a preferred embodiment of the present invention includes an opaque portion 72 disposed in layer 20. Light blocking portion 72 may preferably be disposed along an entire length of layer 20, as shown in FIG. 4. In other embodiments, however, light blocking portion 72 may be disposed at only portions of layer 20 as deemed necessary per particular applications.

As further seen in FIG. 4, light blocking portion 72 is preferably spaced from an inner surface 19 of layer 20, such that a non-opaque layer 74 is formed between inner surface 19 and light blocking portion 72. Such a non-opaque layer 74 is preferably incorporated into flow cell 10 so that radiant energy incident upon inner surface 19 of layer 20 may be received and efficiently reflected or refracted therefrom without significant energy losses. Since radiant energy typically penetrates materials a small degree prior to being reflected or refracted, a non-opaque portion such as layer 74 is preferably provided to minimize absorption of radiant energy incident upon inner surface 19. The depth of penetration of incident radiant energy is dependent upon the material utilized in layer 20. In a particular embodiment wherein layer 20 comprises perfluorinated copolymer, non-opaque layer 74 has a thickness of at least about two wavelengths of the respective radiant energy passing through open channel 18. The thickness of layer 74 is preferably determined by the relationship defined above. Layer 74 is preferably integral with light blocking portion 72, though layer 74 and portion 72 may alternatively be distinct layers disposed immediately adjacent to one another, wherein such adjacent layers may preferably be chemically bonded to one another. In other embodiments, however, such adjacent layers may be juxtaposed adjacent one another without having chemical bonding therebetween.

In a preferred embodiment of the present invention, light blocking portion 72 includes a colorant such as carbon black. A variety of light blocking colorants may be incorporated into portion 72, although carbon has been found to be particularly advantageous when used in combination with perfluorinated copolymer materials in first layer 20. Another light-blocking colorant useful in the present invention is titaniumdioxide ($TiO_2$). The carbon is preferably suspended or dispersed into a perfluorinated copolymer solution at a concentration of between about 0.01–2% by weight carbon. More preferably, the carbon loading is between about 0.1–1% by weight in the perfluorinated copolymer solution. A particular carbon material preferred for use in the present invention is manufactured by Cabot® under the trade name Elftex 12.

Preferably, light blocking portion 72 is formed from a polymeric solution including the desired colorant material. In a particular example, perfluorinated copolymer such as Teflon AF may be dissolved in a commercially available solvent such as Ausimont™ HT-55 or 3M® FC-75. Powdered carbon may then be suspended or dispersed directly into the perfluorinated copolymer solution to form a light blocking polymeric material. One method for forming layer 20 of the present invention provides for extruding the light blocking solution over a preformed tube defined by layer 74. The perfluorinated copolymer in light blocking layer 72 preferably chemically bonds to the perfluorinated copolymer of non-opaque layer 74 to form a continuous first layer 20.

An alternative method for forming layer 20 includes dipping a preformed tube defined by layer 74 into the carbon-loaded perfluorinated copolymer solution such that layer 72 is formed in surrounding relationship to layer 74. Layer 72 preferably chemically bonds to layer 74 to form an integral layer 20 having a light-blocking portion 72. The initial tube 74 may be formed by dipping surface-modified fiber optic tubing into a solution of perfluorinated copolymer, and subsequently removing the fiber optic tubing from within the now-formed perfluorinated copolymer tube 74. Such surface modification may include coating the fiber optic tubing with a stable, non-binding compound such as a poly-imide material.

A preferred method for forming layer 20 having a light-blocking portion 72 integral therewith is through a single-step extrusion process. A polymeric solution, such as perfluorinated copolymer in an appropriate solvent, having between about 0.01 and about 2% by weight carbon suspended or dispersed therein may be extruded over a pin to form a tube of desired dimensions. It has been determined that such a single-step extrusion process extruding a carbon-loaded polymeric material such as perfluorinated copolymer preferably forms an inner portion 74 substantially free of the carbon or other light-blocking material. In such a manner, a single extruded tube having a light-blocking portion 72 in substantially surrounding relationship with a colorant-free portion 74 may be efficiently manufactured through such a single-step extrusion process.

A particular example of this method includes direct mixing in a screw-type extruder. In this method, the perfluorinated copolymer is dry-mixed with an appropriate amount of carbon or other opaquing material, and subsequently fed into the extruder. During the extruder-melting process, the carbon is coated with the perfluorinated copolymer, thus forming a layer during the tubing extrusion process. The extruded tubing includes a layer of a few wavelengths or more of pure perfluorinated copolymer.

Light blocking portion 72 may also be incorporated into second layer 22 and third layer 24 as desired. Similar methods for impregnating the respective layers with light blocking colorant may be utilized.

Figure 5:
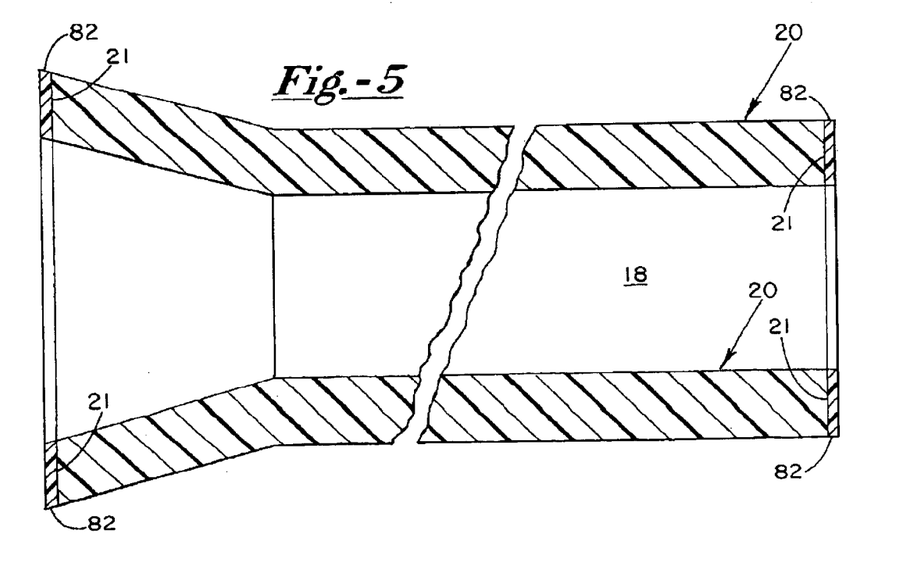
FIG. 5 is a cross-sectional view of tubing having radiant energy-blocking portions disposed at respective end surfaces of the tubing.

In another embodiment of the present invention as illustrated in FIG. 5, pigment-loaded solution as described above may be coated onto end surfaces 21 of first layer 20 to minimize stray light from passing therethrough. Light blocking material 82 may therefore be "painted" on surfaces which may be exposed to radiant energy. Material 82 preferably acts as a block to incoming radiant energy, whereby incident radiant energy is directed through open channel 18. Light blocking material 82 is preferably the same as that used in light blocking portion 72, and may be applied to layers other than, or in addition to first layer 20 as desired. Light blocking layer 82 is preferably sufficiently thick to inhibit incident radiant energy from passing therethrough.

In preferred embodiments of the present invention, a fluid channel 28 is disposed in end cap 14, and extends from said second channel 26 to an exterior surface of end cap 14. As shown in FIG. 1, fluid channel 28 preferably extends through an entire dimension of end cap 14 such that fluid may flow between an exterior surface of end cap 14 and open channel 18 through fluid channel 28. Walls defining fluid channel 28 may be the same material as end cap 14, or may be lined or coated with a different material that may be desired for particular applications.

In the embodiment illustrated in FIG. 1, end cap 16 is preferably similar to end cap 14. End cap 16 preferably includes a third open channel 30 extending therethrough in a plane coincident with a plane associated with open channel 18. Furthermore, end cap 16 preferably includes a fluid channel 32 extending from such third open channel 30 to an exterior surface of end cap 16, thereby providing a flow duct for fluid to pass between open channel 18 and the exterior of end cap 16.

A preferred feature of the embodiment depicted in FIG. 1 is the protrusion 40 extending from the respective end caps 14, 16. Protrusions 40 are adapted to be received in cell body 12 such that a fluid seal is formed at an interface between the cell body and the respective end caps 14, 16. Second and third open channels 26, 30, respectively, preferably extend through protrusions 40 such that respective openings to the second and third open channels are disposed in respective outer surfaces of the protrusions 40. In a particularly preferred embodiment of the present invention, protrusions 40 substantially form conical frustum portions extending from respective end caps 14, 16. As shown in FIG. 1, second and third open channels 26, 30 preferably extend through the frustum portions of said protrusions 40.

The preferred conical frustum shape provides desired fluid sealing characteristics at end cap/cell body interfaces. As shown in FIG. 2, and more clearly in FIG. 3, a section of first layer 20 is flared outwardly. The flared section of first layer 20 is preferably formed by inserting a highly polished heated conical structure into channel 18 defined by first layer 20. In embodiments wherein first layer 20 comprises Teflon AF™, the conical structure is heated to a temperature near a Teflon AF™ glass transition point (240° C.), but under the melting point for Teflon AF™. The heated conical structure therefore forms a portion of first layer 20 to an exterior surface shape of the conical structure.

In some embodiments, first layer 20 is flared to alter an inner dimension of open channel 18 such that fluid may pass to and from open channel 18 more efficiently. The flared section of first layer 20 reduces fluid flow turbulence in channel 18, thereby providing a higher degree of laminar flow. Since fluid flow turbulence causes dispersion in radiant energy passing through the fluid, a reduction in flow turbulence desirably reduces "scattering noise" in photometric analyses of radiant energy transmission, and therefore results in increased spectrophotometric accuracy.

Preferably, an end section 50 of first layer 20 is flared outwardly such that an inner dimension of open channel 18 at end section 50 is substantially equal to a respective inner dimension of open channel 30. By outwardly flaring a portion or rirst layer 20, an inner dimension of open channel 18 may be correspondingly reduced. Such reduction in the internal dimension of open channel 18 correspondingly reduces an inner dimension of first layer 20, which allows a smaller internal volume of open channel 18, thereby reducing sample band spreading in the channel without significant reduction in radiant energy transmission through open channel 18. Furthermore, flared section 50 of first layer 20 enables the reduction of an internal dimension of first layer 20 to less than that of open channel 30 without significant radiant energy losses, due to the angle of inflection between open channel 30 and flared section 50 of channel 18. Such minimum radiant energy loss is possible so long as the flared portion angle combined with the radiant energy angle of incidence is smaller than a radiant energy acceptance angle θ. Such an acceptance angle θ may be determined by the following relationship, where NA is the numerical aperture of channel 18, $n_f$ is the refractive index of the sample fluid, and $n_{fl}$ is the refractive index of the first layer.

$$\mathrm{Sin}\theta = NA = \sqrt{n_f^2 - n_{fl}^2}.$$

Outwardly flared section 50 of first layer 20 is preferably sealingly in intimate contact with a chamfered portion 52 of second layer 22.

As illustrated in FIG. 3, protrusion 40 preferably outwardly displaces a portion of third layer 24 against cell body 12. Such outward displacement creates a latent expansion force in compressed portion 54 of third layer 24. This expansion force preferably assists in securing protrusion 40 in place, and acts to form a fluid seal between protrusion 40 and third layer 24.

Protrusions 40 are illustrated in FIG. 3 as having a generally conical frustum shape, and extending substantially perpendicularly from respective end caps 14, 16. Such a conical frustum shape is preferred for providing desired alignment and sealing characteristics. Conical frustum portions 42 of respective protrusions 40 preferably firmly seat against first layer 20 and displace a portion of the third layer when the respective end caps 14, 16 are assembled to cell body 12 to form flow cell 10. Such displacement provides a relatively high-pressure fluid seal between third layer 24 and protrusion 40. Such a high-pressure seal preferably withstands fluid pressure of up to 2000–3000 pounds per square inch. In addition, the engagement of frustum portions 42 in cell body 12 provides a high-pressure fluid seal at an interface between layers 22 and 24. Frustum portions 42 are preferably arranged to linearly align open channel 18 with respective second and third open channels 26, 30.

The flow cell of FIGS. 1–3 is preferably formed by providing the end caps as described above and a cell body having an open bore extending therethrough. A section of Teflon AF™ tubing is selected for use as the first layer within the open bore. The Teflon AF™ tube may be formed through an extrusion process or any other process that effectively creates such tubing. The Teflon AF™ tube section is then preferably positioned within a section of PEEK tubing, which PEEK tubing forms the second layer within the open bore. In preferred embodiments, the PEEK tube section is in intimate contact with the Teflon AF™ tube. An inner surface of at least one end portion of the PEEK tube section is preferably chamfered outwardly to form a generally conical end portion. A heated cone is subsequently inserted a desired distance into a corresponding portion of the Teflon AF™ tube to flare such Teflon AF™ tube section outwardly against the chamfered portion of the outwardly-disposed PEEK tube. The combination PEEK/Teflon AF™ (PT) tube section is then cut to a precision length in such a manner so as to form a clean cut edge having little or no edge distortions or burrs.

Preferably, a section of FEP tubing is cut to a length which is longer than the PT tube section, and the PT tube section is inserted therein, thereby forming a multiple-layered tube section. The multi-layered tube section is then inserted into the open bore in the cell body. In a preferred embodiment of the present invention, the FEP tube section is heated to a point at which the material is somewhat pliable. The heated tube section is then stretched and thinned, and pulled through the open bore of the cell body, and subsequently cut to a desired length. Once the FEP section has cooled, the PT tube section is inserted into the FEP tube section to thereby form a multi-layered tube assembly within the cell body. Preferably, the PT tube section is friction fit within the FEP tube section.

Once the multi-layered tube assembly positioned within the cell body, the respective end caps are engaged to the cell body such that the protrusions extend at least partially into the open bore. As shown in FIGS. 2 and 3, the protrusions 40 displace a portion of the FEP layer against the cell body, thereby forming a fluid-tight seal between respective protrusions 40 and the FEP layer 24, and between PEEK layer 22 and FEP layer 24. Furthermore, the multi-layered tube assembly is effectively secured between respective end caps 14, 16, and within cell body 40. Preferably, open channel 18, defined by an inner dimension of the Teflon AF™, is in alignment with respective second and third open channels 26, 30 to allow efficient fluid and radiant energy flow through flow cell 10.

As shown in FIG. 3, a gap 60 is preferably left between conical frustum portion 42 of end cap 14 and a respective end of channel 18. In operation, sample fluid fills gap 60, thereby resulting in calculatable radiant energy losses as the radiant energy passes through the fluid-filled gap which is absent the efficient radiant energy transmitting first layer 20. Thus, radiant energy entering gap 60 is allowed to disperse throughout the volume defined by gap 60, causing partial diffusion or loss of the radiant energy. Fluids having relatively higher refractive indexes result in greater degree of radiant energy loss as compared to fluids having relatively lower refractive indexes. Such radiant energy losses may be calculated by the following relationship:

$$E = -10\log\left[1 - \left(a \cdot \frac{NA}{D \cdot nf}\right)\right]$$

where "E" is the radiant energy loss, "a" is the distance between conical frustum portion 42 of end cap 14 and channel 18, defined as gap 60, NA is the numerical aperture of channel 18, D is an internal dimension of channel 18, and $n_f$ is the refractive index of the respective sample fluid. Using such a relationship, a designer of the present invention may select an appropriate gap 60 dimension to offset radiant energy losses for in the first open channel 18 various fluids having different refractive indexes, thereby standardizing such energy losses among the various fluids. Such energy losses inevitably occur in every real open channel 18 due to inherent wall surface imperfections and result in a greater degree of radiant energy loss for fluids having relatively lower refractive indexes as compared to fluids having relatively higher refractive indexes. A typical range for gap 60/channel 18 inner dimension ratio (a/D) is between about 0.1 and about 1.0.

The invention has been described herein in considerable detail in order to comply with the Patent Statutes, and to provide those skilled in the art with the information needed to apply the novel principles and to construct and use embodiments of the invention as required. However, it is to be understood that the invention can be carried out by specifically different devices and that various modifications can be accomplished without departing from the scope of the invention itself.

What is claimed is:

1. A flow cell for transporting fluid in a radiant energy field, comprising:
   a cell structure comprising a first material having a first open channel extending therethrough, and a first elongated tube concentrically disposed around said first open channel, said first tube comprising a second material distinct from said first material, said first tube itself including a radiant energy arresting portion and a radiant energy propagation portion.

2. A flow cell as in claim 1, including a first end cap that is sealingly engagable with said cell structure, said first end cap having a protrusion extending at least partially into said first open channel, and a second open channel substantially aligned with said first open channel to extend the continuous passageway through said first end cap.

3. A flow cell as in claim 2 including a second end cap disposed on, and sealingly engagable with, an opposing end of said cell structure, said second end cap having a protrusion extending at least partially into said first open channel, and a third open channel substantially aligned with said first open channel so as to extend the continuous passageway through said second end cap.

4. A flow cell as in claim 2, including a second tube disposed substantially concentrically about said first tube, and a third tube disposed substantially concentrically around said second tube.

5. A flow cell as in claim 1 wherein said first tube comprises a perfluorinated copolymer.

6. A flow cell as in claim 4 wherein said second tube comprises PEEK.

7. A flow cell as in claim 4 wherein said third tube comprises FEP.

8. A flow cell as in claim 1 wherein said radiant energy arresting portion is disposed along a length of said first tube in surrounding relationship to said radiant energy propagation portion.

9. A flow cell as in claim 8 wherein said radiant energy arresting portion is spaced from an inner surface of said first tube by at least about two wavelengths of the radiant energy.

10. A flow cell as in claim 1 wherein said radiant energy arresting portion is chemically bonded to said first tube.

11. A flow cell as in claim 4 wherein said radiant energy arresting portion is chemically bonded to each of said first, second, and third tubes.

12. A flow cell as in claim 1 wherein said radiant energy arresting portion is disposed at respective end surfaces of said first tube.

13. A flow cell as in claim 1 wherein said radiant energy arresting portion includes carbon.

14. A flow cell as in claim 4 wherein said protrusions of said first and second end caps are positioned to displace respective portions of said third tube, thereby forming a fluid-tight seal between said third tube and said protrusions.

15. A flow cell as in claim 3 wherein said second end cap protrusion is displaced from respective ends of said first tube, whereby a gap volume is formed for fluid residence therein.

16. A flow cell as in claim 15 wherein said gap volume is calibrated such that radiant energy losses may be standardized in respective flow cells transporting fluids having various indexes of refraction.

17. A flow cell as in claim 1 wherein said first tube is formed through a single-step extrusion process.

18. A method of determining sample composition through radiant energy interaction, comprising:
   (a) providing a cell body having an open bore extending therethrough;
   (b) providing one or more layers of material concentrically lining said open bore, at least an innermost one of said layers having a radiant energy arresting portion integral therewith;
   (c) attaching one or more end caps to said cell body, said one or more end caps including protrusions extending therefrom, wherein said protrusions extend at least partially into said open bore such that a fluid-tight seal is formed between said one or more material layers and said protrusions, said end caps further including one or more open channels in substantial alignment with said open bore;
   (d) transporting sample fluid and radiant energy through said open bore such that the radiant energy passes through the sample fluid; and
   (e) receiving and interpreting the radiant energy that has passed through the sample fluid.

19. A method as in claim 18 wherein said radiant energy arresting portion as chemically bonded to at least one of said layers.

20. A method as in claim 18 wherein said radiant energy arresting portion comprises carbon.

* * * * *

UNITED STATES PATENT AND TRADEMARK OFFICE
CERTIFICATE OF CORRECTION

PATENT NO.         : 6,734,961 B2
APPLICATION NO. : 10/068683
DATED              : May 11, 2004
INVENTOR(S)        : Yuri Gerner et al.

Page 1 of 1

It is certified that error appears in the above-identified patent and that said Letters Patent is hereby corrected as shown below:

Claim 4, column 11, line 24, replace "claim 2" with -- claim 3 --.

Signed and Sealed this

Twenty-sixth Day of February, 2008

JON W. DUDAS
*Director of the United States Patent and Trademark Office*